United States Patent [19]

Press et al.

[11] Patent Number: 5,260,453
[45] Date of Patent: Nov. 9, 1993

[54] SUBSTITUTED THIENOPYRANS AS ANTIHYPERTENSIVE AGENTS

[75] Inventors: Jeffrey B. Press, Rocky Hill; Pauline Sanfilippo, Flemington; James J. McNally, High Bridge; Robert Falotico, Belle Mead, all of N.J.

[73] Assignee: Ortho Pharmaceutical Corporation, Raritan, N.J.

[21] Appl. No.: 609,491

[22] Filed: Nov. 5, 1990

Related U.S. Application Data

[62] Division of Ser. No. 249,043, Sep. 23, 1988, Pat. No. 4,992,435.

[51] Int. Cl.$^5$ .................. C07D 223/10; C07D 207/12
[52] U.S. Cl. ..................................... 549/50; 544/377; 546/197; 548/526

[58] Field of Search ............... 549/50; 548/526; 546/197; 544/377

[56] References Cited

U.S. PATENT DOCUMENTS

| 4,036,842 | 7/1977 | Dobson et al. | 549/50 |
| 4,863,922 | 9/1989 | Baldwin et al. | 549/50 |
| 4,992,435 | 2/1991 | Press et al. | 549/50 |
| 5,030,736 | 7/1991 | Press et al. | 549/50 |

Primary Examiner—Alan Siegel
Attorney, Agent, or Firm—John Harbour

[57] ABSTRACT

Substituted thienopyrans and processes for preparing the thienopyrans are disclosed. The thienopyrans are useful as antihypertensive agents; antianginals are peripheral antivasoconstrictive agents 1 Claim, No Drawings

SUBSTITUTED THIENOPYRANS AS ANTIHYPERTENSIVE AGENTS

This is a division of application Ser. No. 249,043, filed Sep. 23, 1988 now U.S. Pat No. 4,992,435.

FIELD OF THE INVENTION

The present invention relates to substituted thienopyran derivatives of the formula:

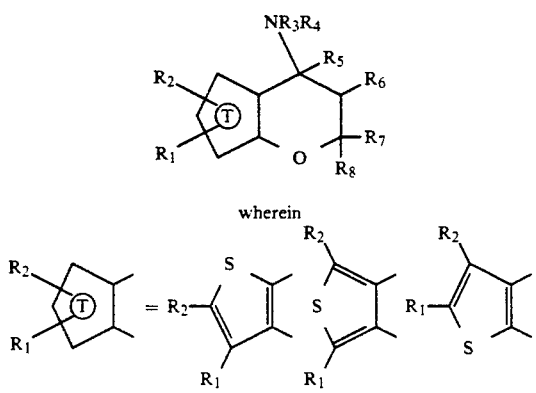

wherein and $R_1$ and $R_2$ are selected from the group consisting of hydrogen, nitro, cyano, trifluoromethyl, halogen such as bromo, chloro, iodo, alkyl ($C_{1-4}$), acyl ($C_{2-4}$), substituted acyl ($C_{2-4}$) (wherein the substituent is halogen such as bromo, chloro, fluoro or iodo), benzoyl, substituted benzoyl (wherein the substituent is halogen such as bromo, chloro, iodo, alkyl ($C_{1-4}$), alkoxy ($C_{1-4}$), acyl ($C_{2-4}$), nirtro, cyano or trifluoromethyl), alkoxy ($C_{1-4}$) carbonyl, CHO, COOH, CONH$_2$, CON(R)$_2$ wherein R is alkyl ($C_{1-4}$), NHCOR wherein R is alkyl ($C_{1-4}$), alkoxy ($C_{1-4}$), phenyl or substituted phenyl [wherein the substituent is halogen such as bromo, chloro, iodo, lower alkyl ($C_{1-4}$), lower alkoxy ($C_{1-4}$), nitro, cyano, trifluoromethyl or lower acyl ($C_{1-4}$)]

$R_3$ and $R_4$ are selected from the group consisting of hydrogen, acyl ($C_{2-5}$), substituted acyl wherein the substituent is CN or CF$_3$ lower alkyl ($C_{1-4}$), cycloalkyl ($C_{3-6}$), cycloalkyl carbonyl ($C_{3-6}$), pyridyl carbonyl, benzoyl, substituted benzoyl [wherein the substituent is halogen such as bromo, chloro, iodo, lower alkyl ($C_{1-4}$), lower alkoxy ($C_{1-4}$), lower acyl ($C_{2-4}$), trifluoromethyl, nitro, cyano RCONH wherein R is alkyl ($C_{1-4}$)] or $R_3R_4N$ together may form a heterocyclic ring such as a pyrrole, pyrrolidine or piperidine ring or a lactam having 3-6 carbon atoms or a glycine anhydride;

$R_5$ is hydrogen or together with $R_6$ forms a double bond;

$R_6$ is hydrogen, hydroxy, alkoxy ($C_{1-6}$), acyloxy ($C_{2-7}$), benzoyl, substituted benzoyl (wherein the substituent is halogen such as bromo, chloro, iodo, lower alkyl ($C_{1-4}$), lower alkoxy ($C_{1-4}$), lower acyl ($C_{2-4}$), nitro, cyano or trifluoromethyl); and $R_7$ and $R_8$ are hydrogen or alkyl ($C_{1-4}$) and together may form a ring having 5-8 carbon atoms.

The substituted thienopyran derivatives are relaxants of smooth muscle tone and as such have utility in vascular tissue for the treatment of hypertensive disease, angina and other vascular disorders characterized by poor regional perfusion (e.g. Raynaud's disease). Other possible utilities include bronchodilation, uterine relaxation, gut motility disorders, and treatment of incontinence. These compounds also are intermediates in possible utilities include bronchodilation, uterine relaxation, gut motility disorders, and treatment of incontinence. These compounds also are intermediates in the preparation of agents having similar pharmacological properties.

DESCRIPTION OF THE PRIOR ART

European Patent Application No. 120 426 describes substituted benzopyrans useful as antihypertensive agents having the following formula:

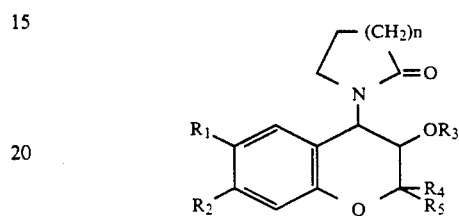

European Patent Application No. 139992 describes substituted benzopyrans useful as antihypertensive agents having the following formula:

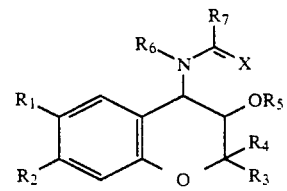

European Patent Application No. 205 292 describes substituted pyrano [3,2-c] pyridine derivatives useful as antihypertensive agents having the following formula:

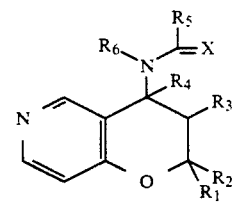

British Patent No. 013786 describes pyrano [3,2-c]pyridine deravatives useful as antihypertensive agents having the following formula:

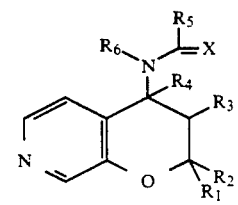

Thiophene analogs of antiviral flavans having the following formula:

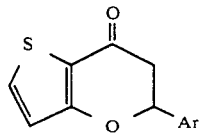

are known in the art [Arch. Pharm. (Weinheim) 318, 70 (1985)].

Thiophene isosteres of flavones and xanthones having the following formula:

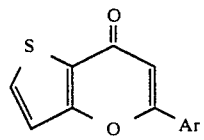

are also known in the art [Tetrahedron, 33, 191 (1977)].

DETAILED DESCRIPTION OF THE INVENTION

The invention in its broadest aspects relates to substituted thienopyrans which are useful are antihypertensives. Several of the intermediates used to make the thienopyrans are also novel compounds and are considered to be part of the invention.

The substituted thienopyrans of this invention are prepared as outlined in Scheme 1.

As can be seen from Scheme 1,3-methoxythiophene (1) Prepared from 3-bromothiophene [S. Gronowitz, Arkiv. Kemi., 1958, 12, 239], is treated with 3,3-disubstituted acryloyl chloride and a Lewis acid catalyst such as tin (IV) chloride, ferric chloride, zinc chloride or the like in an inert solvent such as methylene chloride, chloroform or THF at 0°-25° C. for 1-24 h to give the unsaturated ketone derivative 2. The methoxy group on 2 is cleaved by the action of agents such as boron trifluoride, boron tribromide, boron trichloride, pyridinium hydrochloride or trimethylsilyl iodide in an inert solvent such as methylene chloride or chloroform at −20° to 20° C. to give the alcohol 3. Treatment of 3 with protic acids such as p-toluenesulfonic acid in an inert solvent such as benzene, toluene or the like at reflux temperatures gives the 5,5-disubstituted thieno[3,2-b]pyran-7-one 4. Reduction of the ketone (4) by reducing agents such as sodium borohydride, lithium aluminum hydride or the like in suitable solvents such as alcohols or THF yields the alcohol 5. Dehydration of 5 under acid conditions (p-toluenesulfonic acid, for example) at −20° to 20° C. with molecular sieves in an inert solvent such as dichloromethane, THF or benzene to remove water gives the olefin 6. Alternatively, the ketone (4) may be reduced and the crude, unisolated alcohol (5) may be directly converted to the olefin (6) under similar conditions. Conversion of the olefin (6) to the bromohydrin (7) is accomplished by the action of N-bromosuccinimide and water in solvents such as DMSO or DMF at 0° to 50° C. The bromohydrin (7) is used generally without isolation and treated with bases such as sodium hydride or sodium hydroxide in solvents such as DMSO or DMF at −20° to 20° C. to form the unstable epoxide (8). Anions of amine or amide derivatives are prepared in situ by treating various amines such as pyrrolidine or piperidine or amides such as pyrrolidinone, piperidinone, caprolactam, benzamide and substituted benzamides such as p-nitrobenzamide with sodium hydride in solvents such as DMF or DMSO at room temperature. The epoxide (8) in solvents such as DMF, DMSO or the like is then treated with the thus-formed amine or amide anions at 0° to 20° C. for 1-8 days to form 9 ($R_1R_2$=H). Reaction of 9 with electrophiles such as bromine or nitric acid or the like gives the corresponding substituted thienopyran (9) wherein $R_1R_2$=bromine or nitro, for example. When the electrophile is an acylating agent such as, for example, acetyl chloride or acetic anhydride and the reaction is carried out in the presence of a Lewis acid or protic acid catalyst at about −20° to 20° C. for about 1 hour to 6 days, the product is the acyloxy derivative (10) ($R_1R_2$=H). Similar reactions with the appropriate electrophile under similar conditions produces the acyl acetate (10) ($R_1$ or $R_2$=acyl, for example, acetyl). Reaction of the acetate 10 with methanolic sodium hydroxide or sodium carbonate at about 0°-25° C. for 1-24 hours yields 9 ($R_1$ or $R_2$=acyl, for example, acetyl).

Reaction of 9 with bases such as sodium hydride in solvents such as THF, DMF or the like at 40°-150° C. for 1-16 hours produces enamine (9a).

Alternatively, epoxide 8 is reacted with sodium azide in polar solvents such as DMF or DMSO at about −20° to 100° C. to give azide 9 ($NR_3R_4$=$N_3$). Reduction of the azide with typical hydride reducing agents such a lithium

SCHEME 1

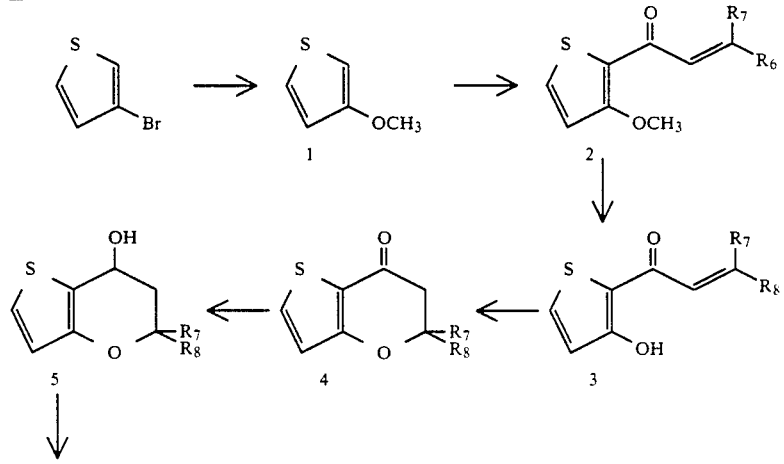

SCHEME 1 -continued

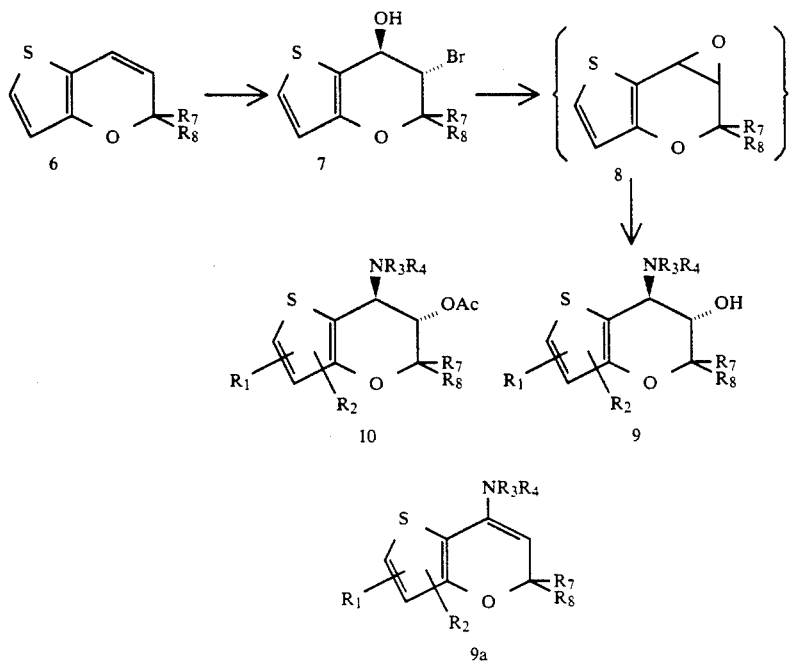

aluminum hydride or sodium borohydride in solvents such as diethyl ether, tetrahydrofuran or alcohols at about 0° to 100° C. or with metals such as zinc or iron in acetic acid or dilute hydrochloric acid gives the corresponding aminoalcohol 9 ($R_3, R_4 = H$). Reaction of this amine with acylating agents such as acetyl chloride, benzoyl chloride or substituted benzoyl chlorides, for example, gives the compounds of the invention 9 wherein $R_3$ or $R_4$ is an acyl group such as acetyl, benzoyl or substituted benzoyl.

Deprotonation of 9 ($R_1R_2=H$) with an agent such as n-butyl lithium, sec-butyl lithium, t-butyl lithium, lithium diisopropylamide or the like in an inert solvent such as THF gives an anion which is reacted with DMF, carbon dioxide or an alkyl chloroformate to give 10 ($R_1R_2=CHO$, $CO_2H$, $CO_2R_9$ where $R_9$=alkyl $C_{1-4}$). Reaction of 10 ($R_1R_2=COOH$) with thionyl chloride produces 10 ($R_1R_2=COCl$) which is reacted with ammonia or amines to produce amides 10 ($R_1R_2=CONH_2$ or $CONHR_9$). Treatment of 10 ($R_1R_2=CONH_2$) with dehydrating agents such as trifluoroacetic anhydride produces 10($R_1R_2=CN$). Treatment of the acetate 10 as before with mild bases produces 9.

The thieno[2,3-b]pyran compounds of this invention are prepared according to Scheme 2. As can be seen from the reaction sequence, 2-methoxythiophene (11) prepared from 2-bromothiophene [Arkiv. Kemi., 1958, 12, 239] is treated with bromine in an inert solvent such as methylene chloride, chloroform or THF at 0° to about 25° C. for about 1–24 h to give the 2,5-disubstituted thiophene (12). Compound 12 is then treated with a 3,3-disubstituted acryloyl chloride and a Lewis acid catalyst such as tin

SCHEME 2

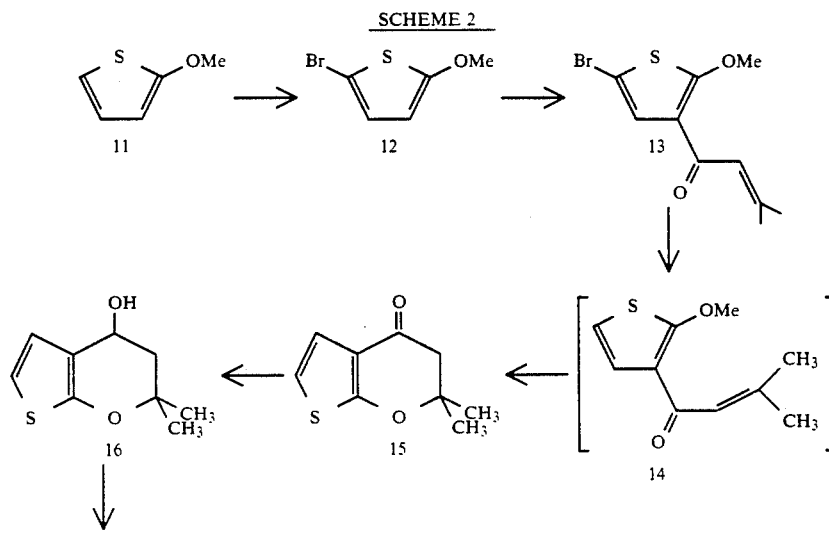

SCHEME 2

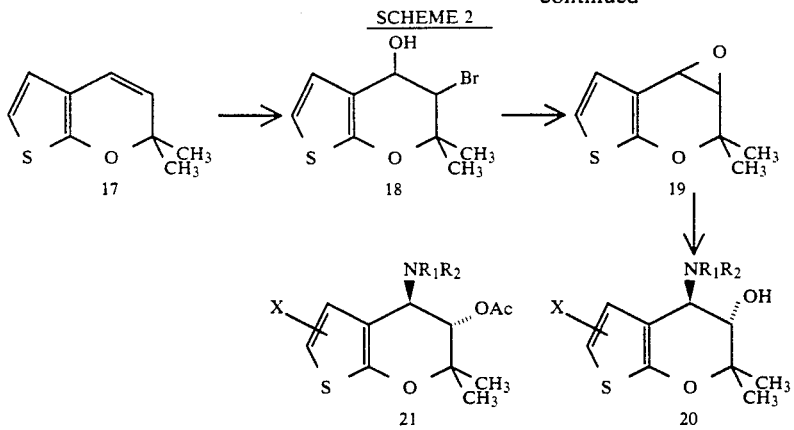

(IV) chloride, ferric chloride, zinc chloride or the like in an inert solvent such as methylene chloride, chloroform or THF at about 0° to 25° C. for about 1-24 h to give the unsaturated ketone derivative (13). The bromine is cleaved by the action of agents such as trialkyltin hydrides [Synthesis, 1970, 10, 499] either neat or in an inert solvent such as ether, benzene or bromobenzene to give 14. The methoxy group is cleaved by the action of agents such as boron trifluoride, boron tribromide, boron trichloride, pyridinium hydrochloride or trimethylsilyl iodide in an inert solvent such as methylene chloride or chloroform at about $-20°$ to $20°$ C. to give the 2-hydroxy-3-substituted thiophene which is not isolated, generally, but is treated with protic acids such as p-toluenesulfonic acid in an inert solvent such as benzene, toluene or the like at about $0°$ to $200°$ C. to give the 3,3-disubstituted thieno[2,3-b]pyran-5-one (15). Using reaction conditions essentially as described in Scheme 1, reduction of the ketone (15) by reducing agents forms alcohol 16. Dehydration of 16 gives the olefin 17. Alternatively, the ketone 15 may be reduced and the crude, unisolated alcohol 16 may be directly converted to 17 under similar conditions. Conversion of 17 to bromohydrin 18 is accomplished by the action of N-bromosuccinimide and water in polar solvents. The bromohydrin is generally used without isolation and treated with bases to form the unstable epoxide 19. Anions of amine or amide derivatives are prepared in situ by treating various amines such as pyrrolidine or piperidine or amides such as pyrrolidinone, piperidinone, caprolactam, benzamide and substituted benzamides such as p-nitrobenzamide with sodium hydride. Epoxide 19 is treated with the thus-formed amine or amide anions to form 20 ($R_1R_2=H$). Reaction of 20 with electrophiles such as bromine or nitric acid or the like gives the substituted compound (20) wherein $R_1R_2=$bromine or nitro, for example. When the electrophile is an acylating agent such as acetyl chloride or acetic anhydride and the reaction is carried out in the presence of a Lewis acid or protic acid catalyst at about $-20°$ to $20°$ C. for 1 hour to 6 days, the product is the acyloxy derivative 21 ($R_1R_2=H$). Further reaction under similar conditions produces the acyl acetate 21 ($R_1$ or $R_2=$acyl, for example, acetyl). Reaction of 21 with methanolic sodium hydroxide or sodium carbonate at about $0°-25°$ C. for 1-24 hours yields the acyl compound (20) ($R_1$ or $R_2=$acyl, for example, acetyl).

Deprotonatin of 20 ($R_1R_2=H$) with an agent such as n-butyllithium, sec-butyl lithium, t-butyl lithium, lithium diisopropylamide or the like in an inert solvent such as THF to give an anion which is reacted with DMF, carbon dioxide or an alkyl chloroformate to give 21 ($R_1R_2=$CHO, $CO_2H$, $CO_2R_9$ where $R_9=$alkyl $C_{1-4}$). Reaction of 21 ($R_1R_2=CO_2H$) with thionyl chloride produces 21 ($R_1R_2=COCl$) which is reacted with ammonia or amines to produce amides 21 ($R_1R_2=CONH_2$ or $CONHR_9$). Treatment of 21 ($R_1R_2=CONH_2$) with dehydrating agents such as trifluoroacetic anhydride produces 21 ($R_1R_2=CN$). Treatment of the acetate 21 as before with mild bases produces 20.

Alternatively, in a manner analogous to scheme 1, epoxide 19 is reacted with sodium azide to give azide 20 ($NR_3R_4=N_3$). Reduction of the azide gives the aminoalcohol 20 ($R_3$, $R_4=H$). Reaction of this amine with acylating agents such as acetyl chloride, benzoyl chloride or substituted benzoyl chlorides, for example, gives the compounds of the invention (20) wherein $R_3$ or $R_4$ is an acyl group such as acetyl, benzoyl or substituted benzoyl.

The thieno[3,4-b]pyrans are prepared according to Scheme 3. In this reaction sequence, 3,4-dibromothiophene is converted by literature procedures [Tetrahedron, 1965, 21, 3331] to 3-bromo-4-t-butoxythiophene (22) which in turn is converted to 3-lithio-4-t-butoxythiophene according to the same literature procedure. Reaction of the 3-lithio compound with a 3,3-disubstituted acryloyl acid derivative such as the methyl or ethyl ester, acid chloride, anhydride or amide derivatives at about $-70°$ to $50°$ C. gives the unsaturated ketone derivative (23). Reaction of 23 with protic acid catalysts such as p-toluenesulfonic acid, sulfuric acid or the like at about $50°-250°$ C. neat or in inert solvents such as toluene or xylenes gives the ring-closed thieno[3,4-]pyranone derivative (24). Using reaction conditions essentially as those described for Scheme 1, reduction of the ketone gives the alcohol 25 which is dehydrated to give the olefin 26. Treatmen of the olefin (26) with N-bromosuccinimide and water in polar solvents gives the bromohydrin 27 which is converted to the epoxide 28. Reaction of 28 with the anions of various amines and amides gives the aminoalcohols 29 ($R_1R_2=H$). Reaction of these derivatives with electrophiles such as bromine, chlorine, sulfuryl chloride or nitric acid gives the substituted derivatives 29 ($R_1$ or $R_2=$Br, Cl, $NO_2$), respectively. When the electrophiles is an acylating agent such as acetyl chloride or acetic anhydride and Lewis or protic acid catalysis is employed, the product is the acetyl acetoxy derivative 30

($R_1$ or $R_2$=acetyl) which may be converted to the aminoalcohol 29 ($R_1$ or $R_2$=acetyl) by treatment with alcoholic base.

SCHEME 3

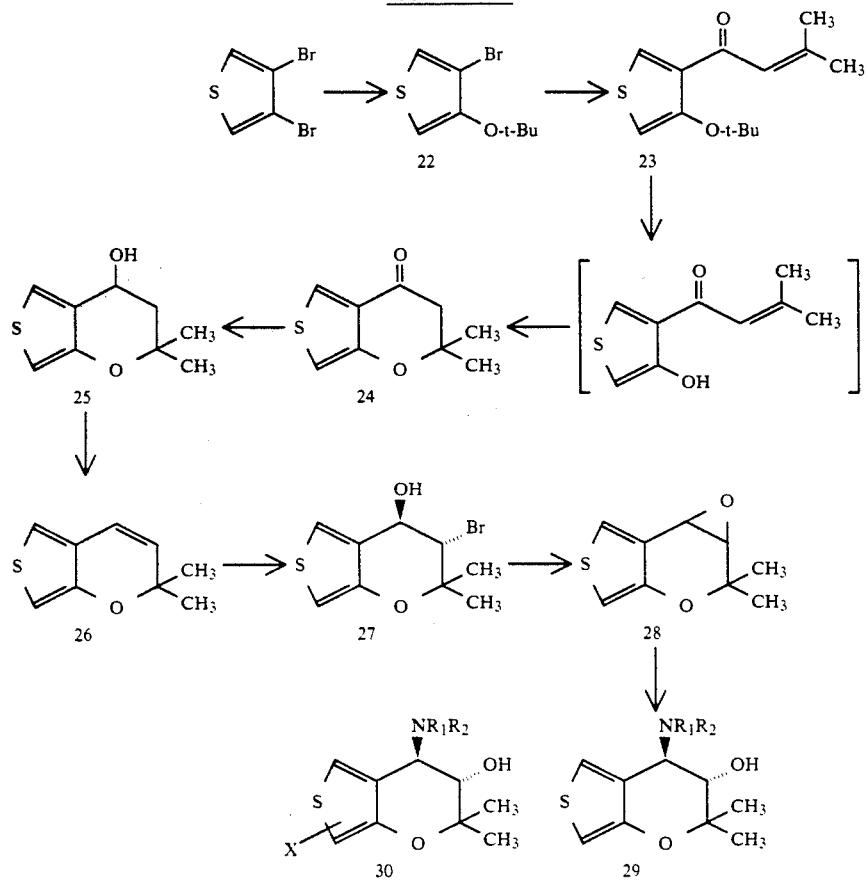

Those compounds wherein $R_7,R_8$=cycloalkyl can be prepared by reacting a cyclic ketone with a Wittig phosphonium ylide reagent to form the 3,3-cycloalkylidine carboxylic acid which is the acrylic acid component of the starting material used to prepare those compounds wherein $R_{71},R_8$=cycloalkyl.

Reaction of 29 with base such as sodium hydride in solvents such as THF, DMF or the like at 40°–150° C. for 1–16 hours produces enamine 29a.

In a manner analogous to that described for Scheme 1, the epoxide 28 may also be reacted with sodium azide in polar solvents to give the azido alcohol 29 ($NR_3R_4=N_3$). This azide is reduced with reducing agents such as hydrides or metals in protic acids to give the aminoalcohol 29 ($R_3,R_4=H$). Reaction of this amine with acylating agents such as acetyl chloride, benzoyl chloride or substituted benzoyl chlorides, for example, gives the compounds of the invention 29 wherein $R_3$ or $R_4$ is an acyl group such as acetyl, benzoyl or substituted benzoyl.

Deprotonation of 29 ($R_1R_2=H$) with an agent such as n-butyl lithium, sec-butyl lithium, t-butyl lithium, lithium diisopropylamide or the like in an inert solvent such as THF gives an anion which is reacted with DMF, carbon dioxide or an alkyl chloroformate to give 30 ($R_1R_2$=CHO, $CO_2H$, $CO_2R_9$ where $R_9$=alkyl $C_{1-4}$). Reaction of 30 ($R_1R_2=CO_2H$) with thionyl chloride produces 30 ($R_1R_2$=COCl) which is reacted with ammonia or amines to produce amides 30 ($R_1R_2$=CONH$_2$ or CONHR$_9$). Treatment of 30 ($R_1R_2$=CONH$_2$) with dehydrating agents such as trifluoroacetic anhydride produces 30 ($R_1R_2$=CN). Treatment of 30 as before with mild bases produces 29.

Reduction of 9 (Scheme 1, $R_1R_2=NO_2$) by catalytic hydrogenation using typical catalysts such as palladium on carbon in the presence of an acylating agent such as acetic anhydride, or benzoyl chloride, for example, in suitable solvents such as acetic acid, for example, yields 9 ($R_1R_2$=NHCR, R=acetyl, benzoyl). In a similar fashion, the reduction of 20 (Scheme 2, $R_1R_2=NO_2$) and 29 (Scheme 3, $R_1$, $R_2=NO_2$) yields the corresponding amide.

The compounds of this invention have antihypertensive activity as determined in spontaneously hypertensive rats (SHR). The compounds also have effects on potassium ion permeability changes within smooth muscle cells as determined in the $Rb^{86}$ efflux assay. [J. M. Smith, A. A. Sanchez and A. W. Jones, Blood Vessels, 1986, 23, 297]

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain, dosage unit, e.g., tablet, capsule, powder, injection, teaspoonful, aerosol and the like, from about 0.1 to about 100 mg/kg and preferably from about 0.1 to about 20 mg/kg of the active ingredient.

The following examples describe the invention in greater particularity and are intended to be a way of illustrating but not limiting the invention.

Best Modes of Carrying out the Invention

Melting point determinations were done on a Thomas Hoover capillary melting point apparatus and are uncorrected. All compounds had spectra (IR, $^1$H NMR, MS) consistent with their assigned structures and were homogeneous by thin layer chromatography. $^1$H NMR were determined on a Brucker Wp-100 FT or a GE QE-300 spectrometer. MS were determined on a Finnigan Mat 8230 using desorption chemical ionization techniques. Silica Gel 60, 230–400 mesh, was used for both flash chromatography and medium pressure chromatography.

EXAMPLE 1

3-Methoxy-2-(3-methyl-1-oxo-2-buten-1-yl)thiophene (2)

A solution of 3-methoxythiophene (21.3 g, 0.187 mol) [S. Gronowitz, Arkiv. Kemi., 1958, 12, 239] in dichloromethane (50 mL) was slowly added to a solution of 3,3-dimethylacryloyl chloride (22 mL, 0.195 mol) and tin(IV) chloride (23 mL, 0.195 mol) in dichloromethane (350 mL) at 0°–5° C. After stirring at 0°–5° C. an additional 1 h, the solution was poured into ice water (1 L). The organic layer was separated, washed with water, and dried over magnesium sulfate. The solvent was evaporated in vacuo. The resulting oil was purified by flash chromatography using dichloromethane as the eluant to give the product, 29.6 g (81%): mp 49°–51° C.; IR (KBr): 1671, 1628 and 1430 cm$^{-1}$; MS: m/z 197 (MH$^+$); $^1$H NMR (CDCl$_3$): δ1.98 (d, J=1.2 Hz, 3H), 2.23 (d, J=1.1 Hz, 3H), 3.98 (s, 3H), 6.85 (d, J=5.5 Hz, 1H), 6.89 (dd, J=1.1 Hz, J=1.2 Hz, 1H) and 7.47 (d, J=5.5 Hz, 1H).

Anal. Calcd. for C$_{10}$H$_{12}$O$_2$S: C, 61.20; H, 6.16; S, 16.34. Found: C, 61.19; H, 6.17; S, 16.31.

3-Hydroxy-2-(3-methyl-1-oxo-2-buten-1-yl)thiophene (3)

A solution of boron trichloride, (1.0M in dichloromethane, 800 mL, 0.80 mol) was slowly added to a solution of 3-methoxy-2-(3-methyl-1-oxo-2-buten-1-yl) thiophene (52.3 g, 0.27 mol) in dichloromethane (400 mL) at −10° C. to 5° C. The resultant solution was stirred an additional 1.5 h at −5° C. Ice water was added slowly with rapid stirring. The organic layer was separated, dried over sodium sulfate, and eluted through a pad of silica gel. The solvent was evaporated in vacuo and the resultant oil was crystallized from hexanes at −70° C. to give the product, 40.0 g (82%), as a yellow solid: mp 32–33° C.; IR (KBr): 1641, 1581 and 1541 cm$^{-1}$; MS: m/z 183 (MH$^+$); $^1$H NMR (CDCl$_3$): δ2.00 (d, J=1.1 Hz, 3H), 2.30 (d, J=1.0 Hz, 3H), 6.25 (m, 1H), 6.75 (d, J=5.3 Hz, 1H), 7.37 (d, J=5.3 Hz, 1H) and 12.14 (s, exchanges with D$_2$O, 1H).

Anal. Calcd. for C$_9$H$_{10}$O$_2$S: C, 59.32; H, 5.54; S, 17.59. Found: C, 59.35; H, 5.51; S, 17.62.

5,6-Dihydro-5,5-dimethyl-7H-thieno[3,2-b]pyran-7-one (4)

A solution of 3-hydroxy-2-(3-methyl-1-oxo-2-buten-1-yl) thiophene (39.0 g, 0.214 mol) and p-toluenesulfonic acid (3.5 g, 18 mmol) in toluene (400 mL) was heated to reflux for 3.5 d. The resultant solution was washed with saturated aqueous sodium bicarbonate and dried over sodium sulfate. The solvent was evaporated in vacuo to give a brown oil, 38.62 g (99%). A portion of the resultant oil was purified for analysis by distillation in a Kugelrohr oven at 145° to 155° C. at 0.35 mm Hg to give the product as an amber oil: IR (neat): 2979, 1664, 1530 and 1442 cm$^{-1}$; MS: m/z 183 (MH$^+$); $^1$H NMR (CDCl$_3$): δ1.51 (s, 6H); 2.67 (s, 2H); 6.67 (d, J=5.4 Hz, 1H) and 7.60 (d, J=5.4 Hz, 1H).

Anal. Calcd. for C$_9$H$_{10}$O$_2$S: C, 59.32; H, 5.54; S, 17.69. Found: C, 59.39; H, 5.53; S, 17.67.

5,6-Dihydro-7-hydroxy-5,5-dimethyl-7H-thieno[3,2-b]pyran (5)

Sodium borohydride (0.97 g, 25.5 mmol) was added to a solution of 5,6-dihydro-5,5-dimethyl-7H-thieno [3,2-b]pyran-7-one (3.1 g, 17.0 mmol) in ethanol (50 mL) and stirred at rt for 2 h. An additional 0.97 g of sodium borohydride was added and the mixture was stirred 16 h. The mixture was poured into water and extracted with dichloromethane. The dichloromethane solution was washed with water (5×) and dried over magnesium sulfate. The solvent was evaporated in vacuo to give the product, 2.96 g (95%), as a brown oil: IR (neat): 3373, 2976, 1561 and 1400 cm$^{-1}$; MS: m/z 185 (MH$^+$); $^1$H NMR (CDCl$_3$): δ 1.34 (s, 3H), 1.45 (s, 3H), 1.87 (m, 1H), 1.94 (d, J=7.0 Hz, 1H, exchanges with D$_2$O), 2.16 (m, 1H), 4.88 (m, 1H), 6.57 (d, J=5.4 Hz, 1H), 7.13 (d, J=5.4 Hz, 1H). This oil was used without further purification in the next step.

5,5-Dimethyl-5H-thieno[3,2-b]pyran (6, Method A)

A mixture of 5,6-dihydro-7-hydroxy-5,5-dimethyl-7H-thieno [3,2-b]pyran (1.3g, 7.06 mmol), p-toluenesulfonic acid (0.11 g, 0.58 mmol) and ground molecular sieves (1.3 g) was stirred at −5° C. for 1.5 h. The mixture was washed with 1.0 N aqueous sodium hydroxide and dried over magnesium sulfate. The solvent was evaporated in vacuo to give the product, 1.17 g (99%), as a red oil: IR (neat): 2976, 1504 and 1531 cm$^{-1}$; MS: m/z 167 (MH$^+$); $^1$H NMR (CDCl$_3$): δ1.45 (s, 6H), 5.27 (d, J=9.8 Hz, 1H), 6.30 (d, J=9.8 Hz, 1H), 6.60 (d, J=5.3 Hz, 1H) and 6.99 (d, J=5.3 Hz, 1H). This oil was used without further purification in the next step.

5,5-Dimethyl-5H-thieno[3,2-b]pyran (6, Method B)

Sodium borohydride (3.27 g, 86.3 mmol) was added to a solution of 5,6-dihydro-5,5-dimethyl-7H-thieno [3,2-b]-pyran-7-one (12.1 g, 66.4 mmol) in ethanol (100 mL) and the resultant mixture was stirred at rt for 17 h. The mixture was poured into water (400 mL) and extracted with dichloromethane (2×100 mL). The dichloromethane solution was washed with water (5×), dried over sodium sulfate, and filtered. Molecular sieves (12 g) and p-toluenesulfonic acid (1.2 g, 6.3 mmol) was added to the resultant solution and stirred at 0° C. for 1.5 h. The reaction mixture was filtered, washed with saturated aqueous sodium bicarbonate and dried over sodium sulfate. The solvent was evaporated in vacuo to give the product, 11.0 g (99%), as a red oil which was identical in all respects to the product described in Method A.

6-Bromo-7-hydroxy-5,6-dihydro-5,5-dimethyl-7H-thieno[3,2-b]pyran (7)

N-Bromosuccinimide (12.9 g, 72.5 mmol) was added in portions to a solution of 5,5-dimethyl-5H-thieno[3,2-b]pyran (10.95 g, 65.9 mmol) and water (1.6 mL, 89.5 mmol) in dimethyl sulfoxide (110 mL) at rt. The resultant solution was stirred at rt for 16 h poured into ice water (400 mL) and extracted into dichloromethane. The dichloromethane solution was washed with water (5×) and dried over sodium sulfate. The solvent was evaporated in vacuo and the residue was purified by flash chromatography using dichloromethane as the eluant to give the product, 11.5 g (66%), as a brown oil: Note that this oil is thermally unstable and decomposes within several hours at rt: $^1$H NMR (CDCl$_3$): δ 1.44 (s, 3H), 1.60 (s, 3H), 2.56 (d, J=4 Hz, 1H, exchanges with D$_2$O), 4.10 (d, J=7 Hz, 1H), 4.98 (dd, J=4 Hz, J=7 Hz, 1H), 6.56 (d, J=5 Hz, 1H), 7.16 (d, J=5 Hz, 1H). This oil was used without further purification in the next step.

5,6-Dihydro-6-hydroxy-5,5-dimethyl-7-(2-oxopyrrolidin-1-yl)-7H-thieno[3,2-b]pyran Sodium hydride (60% in oil, 1.17 g, 29.3 mmol) was added to a solution of 6-bromo-7-hydroxy-5,6-dihydro-5,5-dimethyl-7H-thieno [3,2-b]pyran (7.0 g, 26.6 mmol) in N,N-dimethylformamide (115 mL) at 0° C. The resultant mixture was stirred at rt for 2 h. 2-Pyrrolidinone (6.1 mL, 79.8 mmol) was added to the solution followed by sodium hydride (60% in oil, 1.17 g, 29.3 mmol) and stirring was continued at rt for 4 days. The solution was poured into ice water (500 mL) and extracted with dichloromethane. The dichloromethane solution was washed with water (5×) and dried over sodium sulfate. The solvent was evaporated in vacuo and the resultant solid was triturated in diethyl ether to give the product, 3.91 g (55%), as a colorless solid: mp 154°-155° C.; IR (KBr): 3263, 1665 and 1562 cm$^{-1}$; MS: m/z 268 (MH+); $^1$H NMR (CDCl$_3$): δ 1.30 (s, 3H), 1.50 (s, 3H), 2.07 (m, 2H), 2.52 (m, 2H), 3.00 (d, J=5.5 Hz, 1H, exchanges with D$_2$O), 3.35 (m, 2H), 3.78 (dd, J=5.5 Hz, J=9.0Hz 1H, simplifies to d, J=9.0 Hz, with D$_2$O), 5.28 (d, J=9.0 Hz, 1H), 6.57 (d, 5.4 Hz, 1H) and 7.11 (d, J=5.4 Hz, 1H).

Anal. Calcd. for C$_{13}$H$_{17}$NO$_3$S: C, 58.40; H, 6.41; N, 5.24; S, 11.99.

Found: C, 58.57; H, 6.47; N, 5.23; S, 12.03.

EXAMPLE 2

5,6-Dihydro-6-hydroxy-5,5-dimethyl-7-(2-oxopioeridin-1-yl)7H-thieno[3,2-b]pyran 6-Bromo-7-hydroxy-5,6-dihydro-5,5-dimethyl-7H-thieno[3,2-b]pyran (1.5 g, 5.7 mmol) and δ-valerolactam (1.7 g, 17.1 mmol) were treated with sodium hydride (0.50 g, 12.5 mmol) in N,N-dimethylformamide (25 mL) using the procedure described in Example 1 to give the product as a colorless solid, 0.681 g (43%): mp 151°-152° C.; IR (KBr): 3195, 1610 and 1563 cm$^{-1}$; MS: m/z 282 (MH+); $^1$H NMR (CDCl$_3$): δ1.29 (s, 3H), 1.49 (s, 3H), 1.81 (m, 4H), 2.53 (t, J=6.5 Hz, 2H), 3.15 (m, 1H), 3.24 (m, 1H), 3.68 (d, J=5.0 Hz, 1H, exchanges with D$_2$O), 3.79 (dd, J=5.0 Hz, J=9.1 Hz, 1H, simplifies to d, J=9.1 Hz with D$_2$O), 5.84 (d, J=9.1 Hz, 1H), 6.57 (d, J=5.4 Hz, 1H) and 7.11 (d, J=5.4 Hz, 1H).

Anal. Calcd. for C$_{14}$H$_{19}$NO$_3$S: C, 59.76; H, 6.81; N, 4.98; S, 11.40. Found: C, 59.85; H, 7.05; N, 5.11; S, 11.26.

EXAMPLE 3

5.6-Dihydro-6-hydroxy-5,5-dimethyl-7-(4-nitrobenzamido)-7H-thieno[3,2-b]pyran 6-Bromo-7-hydroxy-5,6-dihydro-5,5-dimethyl-7H-thieno-[3,2-b]-pyran (6.8 g, 25.8 mmol) and 4-nitrobenzamide (10.7 g, 64.5 mmol) were treated with sodium hydride 60% in oil (2.26 g, 56.8 mmol) in N,N-dimethylformamide (110 mL) using the procedure described for the preparation of 5,6-dihydro-6-hydroxy-5,5- dimethyl-7-(2-oxopyrrolidin -1-yl)-7H-thieno[3,2-b]pyran. The reaction mixture was poured into water and extracted into 10% isopropanol in dichloromethane. The solvent was evaporated in vacuo and the residue was purified by medium pressure chromatography using 2% methanol in dichloromethane as the eluant to give the product, 4.5 g (50%), as a pale yellow solid: mp 183°-186° C. dec; IR (KBr): 3398, 1664, 1644 and 1601 cm$^{-1}$; MS: m/z 349 (MH+); $^1$H NMR (CDCl$_3$): δ1.35 (s, 3H), 1.50 (s, 3H), 3.79 (d, J=7.9 Hz, 1H), 4.26 (bs, 1H, exchanges with D$_2$O), 5.19 (d, d, J=7.9 Hz, and J=7.0 Hz, 1H), 6.59 (bd, J=7.0 Hz, 1H, shifts to 6.66 with D$_2$O), 6.63 (d, J=5.4 Hz, 1H), 7.18 (d, J=5.4 Hz, 1H), 7.97 (d, J=8.8 Hz, 2H) and 8.32 (d, J=8.8 Hz, 2H).

Anal. Calcd. for C$_{16}$H$_{16}$N$_2$O$_5$S: C, 55.16; H, 4.63; N, 8.04; S, 9.20. Found: C, 55.45; H, 4.76; N, 8.25; S, 9.14.

EXAMPLE 4

2-Bromo-5,6-dihydro-6-hydroxy-5,5-dimethyl-7-(2-oxopyrrolidin-1-yl)-7H-thieno [3,2-b]pyran A solution of bromine (0.20 mL, 3.92 mmol) in dichloromethane (5 mL) was slowly added to a solution of 5,6-dihydro-6-hydroxy-5,5-dimethyl-7-(2-oxopyrrolidin-1-yl)-7H-thieno[3,2-b]pyran (1.0 g, 3.74 mmol) at −5° C. The resultant mixture was stirred at rt for 2 h. The resulting precipitate was collected by filtration and purified by medium pressure chromatography using 5% methanol in dichloromethane as the eluant to give the product as a colorless solid, 0.28 g (22%): mp 162°-165° C.; IR(KBr): 3287, 1666 and 1570 cm$^{-1}$; MS m/z: 346 (MH+); $^1$H NMR (CDCl$_3$): δ1.30 (s, 3H), 1.47 (s, 3H), 2.06 (m, 2H), 7.50 (m, 2H), 3.23 (bs, 1H, exchanges with D$_2$O), 3.34 (m, 2H), 3.76 (d, J=9.1 Hz, 1H) 5.16 (d, J=9.1 Hz, 1H) and 6.56 (s, 1H).

Anal. Calcd. for C$_{13}$H$_{16}$BrNO$_3$S: C, 45.10; H, 4.66; N, 4.05. Found: C, 45.10; H, 4.40; N, 3.97.

EXAMPLE 5

5,6-Dihydro-6-hydroxy-5,5-dimethyl-2-nitro-7-(2-oxopyrrolidin-1-yl)-7H-thieno [3,2-b]pyran Nitric acid (90%, 1.2 mL, 26.9 mmol) was added to a solution of 5,6- dihydro-6-hydroxy-5,5-dimethyl-7-(2-oxopyrrolidin-1-yl)-7H-thieno[3,2-b]pyran (1.0 g, 3.74 mmol]in acetic acid (30 mL) at 18° C., and stirred at rt for 1.5 h. The resultant solution was poured into ice water (200 mL). Within 10 min a yellow solid crystallized which was collected by filtration, washed with water and triturated in diethyl ether to give the product, 0.487 g (42%), as a yellow solid: mp 214°-217° C.; IR (KBr): 3216, 1655 and 1512 cm$^{-1}$; MS: m/z 313 (MH+); 1H NMR (DMSO-d$_6$): δ1.23 (s, 3H), 1.43 (s, 3H), 2.00 (m, 2H), 2.36 (m, 2H), 3.16 (m, 1H), 3.20 (m, 1H), 3.80 (d, J=9.5 Hz, 1H), 4.98 (d, J=9.5 Hz, 1H), 5.92 (bs, 1H, exchanges with D$_2$O) and 7.75 (s, 1H).

Anal. Calcd. for $C_{13}H_{16}N_2O_5S$: C, 49.99; H, 5.16; N, 8.97; S, 10.27. Found: C, 49.70; H, 5.00; N, 8.65; S, 10.33.

EXAMPLE 6

6-Acetoxy-2-acetyl-5,6-dihydro-5,5-dimethyl-5-(2-oxopyrrolid-1-yl)-7H-thieno [3,2-b]]pyran A solution of 5,6-dihydro-6-hydroxy-5,5-dimethyl-7-(2-oxopyrrolidin-1-yl)- 7H-thieno[3,2-b]pyran 1.76 g, 6.58 mmol) and perchloric acid (70%, 10 drops) in acetic anhydride (15 mL) was stirred at 60° C. for 2 h. The resultant brown solution was poured into ice water (100 mL) and the product was extracted into dichloromethane, washed with water (4×) and dried over sodium sulfate. The solvent was evaporated in vacuo and the resultant oil was purified by medium pressure chromatography using 1% methanol in dichloromethane as the eluant to give the product, 0.85 g (37%): mp 170°-172° C.; IR (KBr): 1755, 1690, 1666 and 1564 cm$^{-1}$; MS: m/z 352 (MH+); 1H NMR (CDCl$_3$): δ 1.38 (s, 3H), 1.39 (s, 3H), 1.98 (m, 2H), 2.10 (s, 3H), 2.37 (m, 2H), 2.49 (s, 3H), 3.23 (m, 1H), 3.38 (m 1H), 5.14 (d, J=9.3 Hz, 1H), 5.47 (d, J=9.3 Hz, 1H) and 7.16 (s, 1H).

Anal. Calcd. for $C_{17}H_{21}NO_5S$: C, 58.10; H, 6.02; N, 3.99; S. 9.12. Found: C, 57.76; H, 5.87; N, 3.69; S, 9.11.

EXAMPLE 7

2Acetyl-5,6-dihydro-6-hydroxy-5,5-dimethyl-7-(2-oxopyrrolidin-1-yl)-7H-thieno [3,2-b]pyran Aqueous sodium hydroxide (50%, 0.15 g, 1.87 mmol) was added to a solution of 6-acetoxy-2-acetyl-5,6-dihydro-5,5-dimethyl-7-(2-oxopyrrolidin-1-yl)-7H-thieno[3,2-b]pyran (0.45 g, 1.28 mmol) in methanol (20 mL) and stirred at rt for 1 h. The solution was poured into water (100 mL) and extracted into dichloromethane. The dichloromethane solution was washed with water (3×) and dried over magnesium sulfate. The solvent was evaporated in vacuo and the resultant oil was crystallized from diethyl ether and hexanes to give the product, 0.327 g (83%), as a colorless solid: mp 102°-106° C.; IR (KBr): 1665 and 1561 cm$^{-1}$; MS: m/z 310 (MH+); 1H NMR (CDCl$_3$): δ 1.31 (s, 3H), 1.51 (s, 3H), 2.07 (m, 2H), 2.48 (s, 3H), 2.51 (m, 2H), 3.34 (m, 2H), 3.45 (d, J=6.2 Hz, 1H, exchanges with D$_2$O), 3.80 (dd, J=6.2 Hz and J=9.4 Hz, 1H, simplifies to d, J=9.4 Hz, with D$_2$O), 5.29 (d, J=9.4 Hz, 1H) and 7.14 (s, 1H).

Anal. Calcd. for $C_{15}H_{19}NO_4S$: C, 58.23; H, 6.19; N, 4.53. Found: C, 58.30; H, 6.31; N, 4.45.

EXAMPLE 8

Acetoxy-5,6-dihydro-5,5-dimethyl-7-(2-oxopyrrolidin-1-yl)-7H-thienol[3,2-b]pyran A solution of 5,6-dihydro-6-hydroxy-5,5-dimethyl-7-(2-oxopyrrolidin-1-yl)-7H-thieno[3,2-b]pyran (2.0 g, 7.48 mmol) and perchloric acid (70%, 10 drops) in acetic anhydride (20 mL) were stirred for 1 h at 0°-5° C. The solution was poured into ice water (100 mL). The product was extracted into dichloromethane, washed with water (4×), and evaporated in vacuo. The resultant oil was purified by flash chromatography, using 1% methanol in dichloromethane as the eluant, then crystallized from hexanes to give the product, 2.12 g (92%), as a colorless solid: mp 92°-93° C.; IR(KBr): 1745 and 1684 cm$^{-1}$; MS: 310 (MH+); 1H NMR (CDCl$_3$): δ 1.37 (s, 3H), 1.38 (s, 3H), 1.98 (m, 2H), 2.10 (s, 3H), 2.37 (m, 2H), 3.24 (m, 1H), 3.40 (m, 1H), 5.15 (d, J=9.1 Hz, 1H), 5.44 (d, J=9.1 Hz, 1H), 6.58 (d, J=5.4 Hz, 1H) and 7.13 (d, J=5.4 Hz, 1H).

Anal. Calcd. for $C_{15}H_{19}NO_4S$: C, 58.23; H, 6.19; N, 4.52; S, 10.36. Found: C, 58.11; H, 5.89; N, 4.31; S, 10.41.

EXAMPLE 9

5,6-Dihydro-6-hydroxy-5,5-dimethyl-2-nitro-7-(4-nitrobenzamido)-7H-thieno[3,2-b]pyran 5,6-Dihydro-6-hydroxy-5,5-dimethyl-7-(4-nitrobenzamido)-7H-thieno[3,2-b]pyran (1.5 g, 4.30 mmol) was treated with 90% nitric acid (2.5 mL, 53.5 mmol) in acetic acid (25 mL) and stirred at 15°-20° C. for 0.5 h. The resultant solution was poured into ice water 100 mL and extracted with 10% isopropanol in dichloromethane. The dichloromethane solution was washed with saturated aqueous sodium bicarbonate and dried over magnesium sulfate. The solvent was evaporated in vacuo and the residue was purified by medium pressure chromatography using 2% methanol in dichloromethane as the eluant, to give the product, 0.489 g (29%), as a yellow solid: mp 221°-225° C. dec; IR (KBr): 3345, 1647 and 1602 cm$^{-1}$; MS: m/z 394 (MH+); 1H NMR (DMSO-d$_6$): δ 1.26 (s, 3H), 1.45 (s, 3H), 3.90 (dd, J=8.8 Hz and J=5.9 Hz, 1H, simplifies to d, J=8.8 Hz with D$_2$O), 4.98 (dd, J=7.6 Hz and J=8.8 Hz, 1H, simplifies to d, J=8.8 Hz with D$_2$O), 6.01 (d, J=5.9 Hz, 1H exchanges with D$_2$O), 7.75 (s, 1H), 8.14 (d, J=8.8 Hz, 2H) 8.37 (d, J=8.8 Hz, 2H) and 9.38 (d, J=7.6 Hz, 1H, exchanges with D$_2$O).

Anal. Calcd. for $C_{16}H_{15}N_3O_7S$: C, 48.85; H, 3.84; N, 10.68. Found: C, 48.91; H, 3.62; N, 10.46.

EXAMPLE 10

5.6-Dihydro-6-hydroxy-5,5-dimethyl-2-nitro-7-(2-oxopiperidin-1-yl)-7H-thieno3,2-b]pyran The title compound was prepared as described in Example 5 starting with 5,6-dihydro-6-hydroxy-5,5-dimethyl-7-(2-oxopiperidin-1-yl)-7H-thieno[3,2-b]pyran (1.5 g, 5.33 mmol) and 90% nitric acid (2.5 mL) in acetic acid (25 mL) to give the product, 0.837 g (48%), as a yellow solid: mp 210°-211° C.: IR (KBr): 3231, 1613, 1515 and 1492 cm$^{-1}$; MS: m/z 327 (MH+); 1H NMR (CDCl$_3$): δ 1.32 (s, 3H), 1.51 (s, 3H), 1.84 (m, 4H), 2.55 (m, 2H), 3.20 (m, 2H), 3.84 (d, J=9.5 Hz, 1H), 4.78 (bs, 1H, exchanges with D$_2$O), 5.86 (d, J=9.5 Hz, 1H) and 7.40 (s, 1H).

Anal Calcd. for C$_{14}$H$_{18}$N$_2$O$_5$S: C, 51.52; H, 5.56; N, 8.58; S, 9.86. Found: C, 51.26; H, 5.25; N, 8.32; S, 9.86.

EXAMPLE 11

2-Bromo-5,6-dihydro-6-hydroxy-5,5-dimethyl-7-(2-oxopiperidin-1-yl)-7H-thieno[3,2-b]pyran The title compound was prepared as described in Example 4 starting with 5,6-dihydro-6-hydroxy-5,5-dimethyl-7-(2-oxopiperidin-1-yl)-7H-thieno[3,2-b]pyran (1.4 g, 5.0 mmol) and bromine (0.27 mL, 5.2 mmol) in dichloromethane (30 mL). Purification by flash chromatography using 1% methanol in dichloromethane as the eluant and recrystallization from dichloromethane/hexanes gave the product, 3.87 g (78%), as a colorless solid: mp 200°-202° C.; IR(KBr): 3442, 2942, 1616, 1571 and 1488 cm$^{-1}$; MS: m/z 360 (MH+); $^1$H NMR(CDCl$_3$): δ 1.29 (s, 3H), 1.46 (s, 3H), 1.82 (m, 4H), 2.51 (m, 2H), 3.12 (m, 1H), 3.27 (m, 1H), 3.46 (d, J=5.0 Hz, 1H, exchanges with D$_2$O), 3.78 (d,d, J=9.0 Hz, J=5.0 Hz, 1H, simplifies to d, J=9.0 Hz, with D$_2$O), 5.74 (d, J=9.0 Hz, 1H) and 7.58 (s, 1H).

Anal. Calcd. for C$_{14}$H$_{18}$BrNO$_3$S: C, 46.67; H, 5.04; N, 3.89. Found: C, 46.99; H, 5.05; N, 3.84.

EXAMPLE 12

6-Acetoxy-2-acetyl-5,6-dihydro-5,5-dimethyl-7-(4-nitrobenzamido)-7H-thieno[3,2-b]pyran The title compound was prepared as described in Example 6 starting with 5,6-dihydro-6-hydroxy-5,5-dimethyl-7-(4-nitrobenzamido)-7H-thieno[3,2-b]pyran (1.5 g, 4.31 mmol), acetic anhydride (15 mL) and perchloric acid (70%, 10 drops) to give the product, 0.86 g (46%), as a pale yellow solid: mp 251°-253° C. dec; IR (KBr): 1753, 1670, 1655 and 1530 cm$^{-1}$; MS: m/z 433 (MH+); $^1$H NMR (CDCl$_3$): δ 1.41 (s, 3H), 1.44 (s, 3H), 2.14 (s, 3H), 2.48 (s, 3H), 5.18 (d, J=9.3 Hz, 1H), 5.40 (d,d, J=8.3 Hz, J=9.3 Hz, 1H), 6.83 (d. J=8.3 Hz, 1H, shifts to d 6.91 with D$_2$O), 7.14 (s, 1H); 7.94 (d, J=7.1 Hz, 2H), 8.30 (d, J=7.1 Hz, 2H).

Anal. Calcd. for C$_{20}$H$_{20}$N$_2$O$_7$S: C, 55.55; H, 4.66; N, 6.48; S, 7.41. Found: C, 55.34; H, 4.69; N, 6.44; S, 7.31.

EXAMPLE 13

2-Acetyl-5,6-dihydro-6-hydroxy-5,5-dimethyl-7-(4-nitrobenzamido)-7H-thieno[3,2-b]pyran 6-Acetoxy-2-acetyl-5,6-dihydro-5,5-dimethyl-7-(4-nitrobenzamido)-7H-thienopyran (0.60 g, 1.39 mmol) was treated with aqueous sodium hydroxide (1N, 1.5 mL, 1.5 mmol) in methanol (10 mL) at rt and stirred for 2 h. The resultant solution was poured into water and extracted with 5% isopropanol in dichloromethane. The organic phase was washed with water (3×) and dried over magnesium sulfate. The solvent was evaporated in vacuo and the resultant solid triturated in diethyl ether to give the product, 0.36 g (66%), as a pale yellow solid: mp 223°-225° C.; IR (KBr) 1647, 1601, 1530 and 1458 cm$^{-1}$; MS: m/z 391 (MH+); $^1$H NMR (DMSO-d$_6$): δ 1.23 (s, 3H), 1.42 (s, 3H), 2.45 (s, 3H), 3.84 (m, 1H, simplifies to d, J=8.9 Hz with D$_2$O), 5.01 (m, 1H, simplifies to d, J=8.9 Hz, with D$_2$O), 5.86 (d, J=5.9 Hz, 1H, exchanges with D$_2$O), 7.47 (s, 1H), 8.14 (d, J=8.8 Hz, 2H), 8.36 (d, J=8.8 Hz, 2H) and 9.27 (d, 1H, exchanges with D$_2$O).

Anal. Calcd. for C$_{18}$H$_{18}$N$_2$O$_6$S: C, 55.38; H, 4.65; N, 7.18; S, 8.21. Found: C, 55.12; H, 4.63; N, 6.93; S, 8.11.

EXAMPLE 14

7-(4-Chlorobenzamido)-5,6-dihydro-6-hydroxy-5,5-dimethyl-7H-thieno[3,2-b]pyran

The title compound was prepared as described in Example 3 starting with 6-bromo-7-hydroxy-5,6-dihydro-5,5-dimethyl-7H-thieno[3,2-b]pyran (4.75 g, 18.1 mmol) and 4-chlorobenzamide (7.0 g, 45 mmol) in N,N-dimethylformamide (125 mL) to give 1.41 (23%) as a yellow solid: mp 196°-197° C.; IR (KBr): 3483, 3317, 1632 and 1525 cm$^{-1}$; MS: m/z 338 (MH+); $^1$H NMR (DMSO-d$_6$): δ 1.20 (s, 3H), 1.39 (s, 3H), 3.79 (m, 1H, simplifies to d, J=8.8 Hz, with D$_2$O), 4.98 (m, 1H, simplifies to d, J=8.8 Hz with D$_2$O), 5.64 (d, J=6.0 Hz, 1H, exchanges with D$_2$O), 6.58 (d, J=5.3 Hz, 1H), 7.29 (d, J=5.3 Hz, 1H), 7.56 (d, J=6.8 Hz, 2H), 7.93 (d, J=6.8 Hz, 2H) and 8.88 (d, J=8.3 Hz, 1H, exchanges with D$_2$O).

Anal. Calcd. for C$_{16}$H$_{16}$ClNO$_3$S: C, 56.89; H, 4.77; N, 4.15. Found: C, 56.72; H, 4.68; N, 4.00.

EXAMPLE 15

7-(4-Chlorobenzamido)-5,6-dihydro-6-hydroxy-5,5-dimethyl-2-nitro-7H-thieno[3,2-b]pyran The title compound was prepared as described in Example 9 starting with 7-(4-chlorobenzamido)-5,6-dihydro-6-hydroxy-5,5-dimethyl-7H-thieno[3,2-b]pyran (1.23 g, 3.64 mmol) and 90% nitric acid (1.5 mL) in acetic acid (20 mL) to give the product, 0.384 g (28%), as a yellow solid: mp 226°-229° C. dec; IR (KBr): 3315, 1655, 1535 and 1503 cm$^{-1}$; MS: m/z 383 (MH+); $^1$H NMR (DMSO-d$_6$): δ 1.25 (s, 3H), 1.44 (s, 3H), 3.90 (m, 1H, simplifies to d, J=8.9 Hz with D$_2$O), 4.95 (m, 1H, simplifies to d, J=8.9 Hz, with D$_2$O), 5.94 (d, J=6.0 Hz, 1H exchanges with D$_2$O), 7.60 (d, J=8.6 Hz, 2H), 7.72 (s, 1H), 7.94 (d, J=8.6 Hz, 2H) and 9.11 (d, J=7.6 Hz, 1H, exchanges with D$_2$O).

Anal. Calcd. for C$_{16}$H$_{15}$ClN$_2$O$_5$S: C, 50.20; H, 3.94; N, 7.32; Cl, 9.61; S, 8.69. Found: C, 50.34; H, 3.75; N, 7.00; Cl, 9.36; S, 8.74.

EXAMPLE 16

5,6-Dihydro-6-hydroxy-5,5-dimethyl-7-(4-trifluoromethylbenzamido)-7H-thieno[3,2-b]pyran The title compound was prepared as described in Example 3 starting with 6-bromo-7-hydroxy-5,6-dihydro-5,5-dimethyl-7H-thieno[3,2-b]pyran (4.5 g, 17.1 mmol) and 4-trifluoromethylbenzamide (7.43 g, 39.3 mmol) in N,N-dimethylformamide (75 mL) to give the product, 1.96 g (31%), as a colorless solid: mp 162°-163° C.; IR (KBr): 3396, 1664, 1534 and 1507 cm$^{-1}$; MS: m/z 372 (MH+); $^1$H NMR (DMSO-d$_6$): δ 1.21 (s, 3H), 1.40 (s, 3H), 3.80 (m, 1H, simplifies to d, J=8.7 Hz, with D$_2$O), 5.01 (m, 1H, simplifies to d, J=8.7 Hz, with D$_2$O), 5.68 (d, J=6.0 Hz, 1H, exchanges with D$_2$O), 6.59 (d, J=5.7 Hz, 1H), 7.31 (d, J=5.7 Hz, 1H), 7.88 (d, J=8.3 Hz, 2H), 8.11 (d, J=8.3 Hz, 2H) and 9.05 (d, J=8.4 Hz, 1H exchanges with D$_2$O).

Anal. Calcd. for : C$_{17}$H$_{16}$F$_3$NO$_3$S: C, 54.98; H, 4.34; N, 3.77. Found: C, 55.01; H, 4.28; N, 3.70.

EXAMPLE 17

5,6-(Dihydro-6-hydroxy-2-nitro-7-(4-trifluoromethylbenzamido)-7H-thieno[3,2-b]pyran The title compound was prepared as described in Example 9 starting with 5,6-dihydro-6-hydroxy-7-(4-trifluoromethylbenzamido)-7H-thieno[3,2-b]pyran (1.5 g, 4.04 mmol) and 90% nitric acid (2.5 mL) in acetic acid (20 mL) to give a yellow solid, 0.165 g (10%): mp 219°-220° C.; IR (KBr): 3310, 1661, 1538 and 1504 cm$^{-1}$, MS: m/z 417 (MS+) $^1$H NMR (DMSO-d$_6$): δ 1.26 (s, 3H), 1.45 (s, 3H), 3.92 (m, 1H, simplifies to d, J=8.9 Hz, with D$_2$O), 4.98 (m, 1H, simplifies to d, J=8.9 Hz, with D$_2$O), 5.99 (d, 1H, exchanges with D$_2$O), 7.74 (s, 1H), 7.92 (d, J=8.5 Hz, 2H), 8.12 (d, J=8.5 Hz, 2H) and 9.30 (d, 1H, exchanges with D$_2$O).

Anal. Calcd. for C$_{17}$CH$_{15}$F$_3$N$_2$O$_5$S: C, 49.03; H, 3.63; N, 6.73 Found: C, 49.01; H, 3.27; N, 6.60.

EXAMPLE 18

5,6-Dihydro-6-hydroxy-5,5-dimethyl-7-pyrrolidin-1yl-7H-thieno[3,2-b]pyran

Sodium hydride (60% in mineral oil, 0.145 g, 3.64 mmol) was added to a solution of 6-bromo-5,6-dihydro-7-hydroxy7H-thieno[3,2-b]pyran (0.87 g, 3.31 mmol) in N,N-dimethylformamide (30 mL) at 5° C. The resultant solution was stirred at rt for 1.5 h. Pyrrolidine (0.91 mL, 10.9 mmol) was added to the solution and stirred at rt for 17 h. The solution was poured into ice water, and the product was extracted into diethyl ether, washed several times with water and saturated aqueous sodium chloride, and dried over magnesium sulfate. The solvent was evaporated in vacuo and the residue was purified by flash chromatography using 5% methanol in dichloromethane as the eluant to give the product, 0.55 g (66%), as a yellow solid: mp 85°-89° C.; IR (KBr): 3540, 2970, 2965, 1551 and 1394 cm$^{-1}$; MS: m/z 254 (MH+); $^1$H NMR (CDCl$_3$): δ 1.22 (s, 3H), 1.50 (s, 3H), 1.83 (m, 4H), 2.85 (m, 4H), 3.27 (bs, 1H, exchanges with D$_2$O), 3.62 (d, J=9.3 Hz, 1H), 3.90 (d, J=9.3 Hz, 1H), 6.59 (d, J=5.4 Hz, 1H) and 7.03 (d, J=5.4 Hz, 1H).

Anal. Calcd. for C$_{13}$H$_{19}$NO$_2$S: C, 61.63; H, 7.56; N, 5.53; S, 12.66. Found: C, 61.38; H, 7.60; N, 5.48; S, 12.58.

EXAMPLE 19

6-Hydroxy-5,5-dimethyl-7-(2-oxohexamethyleneimin-1-yl)-7H-thieno[3,2-b]pyran

The title compound was prepared as described for Example 3 starting with the bromoalcohol (2.5 g, 9.5 mmol) and caprolactam (2.1 g, 19.0 mmol) to give 1.35 g (48%): mp 153°-154° C.; IR (KBr): 3200, 1615, 1523 cm$^{-1}$; MS: m/z 296 (MH+); $^1$H NMR (CDCl$_3$): δ 7.13 (d, J=5.4 Hz, 1H), 6.58 (d, J=5.4 Hz, 1H), 5.75 (d, J=9.2 Hz, 1H), 3.69 (m, 1H), 3.36 (d, J=4.9 Hz, 1H), 3.23 (m, 2H), 2.64 (m, 2H), 1.86 (m, 6H), 1.47 (s, 3H), 1.29 (s, 3H).

Anal. Calcd. for C$_{15}$H$_{21}$NO$_3$S: C, 60.99; H, 7.17; N, 4.74; S, 10.85. Found: C, 60.76; H, 6.93; N, 4.76; S, 10.66.

EXAMPLE 20

6-Hydroxy-5,5-dimethyl-2-nitro-7-(2-oxohexamethyleneimin-1-yl)thieno[3,2-b]pyran The title compound was prepared as described for Example 5 starting with 6-hydroxy-5,5-dimethyl-7-(2-oxohexamethyleneimin-1-yl)thieno[3,2-b]pyran (0.5 g, 1.7 mmol) and nitric acid (90%, 0.55 mL, 12.3 mmol) in acetic acid (15 mL) to give 410 mg (71%): mp 218°-219° C.; IR (KBr): 3340, 1627, 1503 cm$^{-1}$; MS: m/z 341 (MH+); $^1$H NMR (CDCl$_3$): δ 7.40 (s, 1H), 5.80 (bd, 1H), 3.73 (d, J=9.5 Hz, 1H), 3.28 (m, 4 H), 2.66 (m, 2 H), 1.87 (m, 4 H), 1.50 (s, 3H), 1.32 (s, 3H).

Anal. Calcd. for C$_{15}$H$_{20}$N$_2$O$_5$S: C, 52.93; H, 5.92; N, 8.23. Found: C, 52.71; H, 5.74; N, 7.84.

EXAMPLE 21

6-Acetoxy-5,5-dimethyl-7-(2-oxohexamethyleneimin-1-yl)-thieno-[3,2-b]pyran

The title compound was prepared as described for Example 8 starting with 6-hydroxy-5,5-dimethyl-7-(2-oxohexamethyleneiminyl)thieno[3,2-b]pyran (1.5 g, 5.1 mmol) and 70% perchloric acid (10 drops) in acetic anhydride (15 mL) to give 1.5 g (87%): mp 153°-154° C.; IR (KBr): 1668, 1615, 1563 cm$^{-1}$; MS: m/z 338 (MH+); $^1$H NMR (CDCl$_3$): δ 7.11 (d, J=5.3 Hz, 1H), 6.57 (d, J=5.3 Hz, 1H), 5.99 (d, J=9.0 Hz, 1H), 5.10 (d, J=9.0 Hz, 1H), 3.16 (m, 2H), 2.52 (m, 2H), 2.09 (s, 3H), 1.66 (m, 6H), 1.36 (s, 3H), 1.34 (s, 3H).

Anal. Calcd. for C$_{17}$H$_{23}$NO$_4$S: C, 60.51; H, 6.87; N, 4.15. Found: C, 60.71; H, 6.54; N, 3.76.

EXAMPLE 22

6-Hydroxy-5,5-dimethyl-7-(2,5-dioxopiperazin-1-yl)-7H-thieno[3,2-b]pyran

The title compound was prepared as described for Example 3 starting with the bromoalcohol (2.5 g, 9.5 mmol) and glycine anhydride (2.2 g, 19.0 mmol) to give 0.58 g (36%); mp 132°-133° C.; IR (KBr): 3210, 1627, 1510 cm$^{-1}$; MS: 297 (MH+) $^1$H NMR (CDCl$_3$): δ 7.13 (d, J=5.4 Hz, 1H), 6.58 (d, J=5.4 Hz, 1H), 5.77 (d, J=9.2 Hz, 1H), 3.54 (m, 1H), 3.46 (d, J=4.9 Hz, 1H), 3.23 (s, 2H), 2.79 (s, 2H), 1.48 (s, 3H), 1.31 (s, 3H).

Anal. Calcd. for C$_{13}$H$_{16}$N$_2$O$_4$S: C, 52.69; H, 5.44; N, 9.45. Found: C, 52.53; H, 5.23; N, 9.67.

EXAMPLE 23

5,6-Dihydro-6-hydroxy-5,5-dimethyl-7-piperidin-1-yl-7H-thieno[3,2-b]pyran

The title compound was prepared as described in Example 18 starting with 6-bromo-5,6-dihydro-7-hydroxy-5,5-dimethyl-7H-thieno[3,2-b]pyran (1.5 g, 5.7 mmol) and piperidine (1.7 mL, 17.1 mmol) in N,N-dimethylformamide (25 mL) to give an off white solid, 0.977 (64%): mp 68°-70°C.; IR (KBr): 2937, 1549 and 1396 cm$^{-1}$; MS: m/z 162 (MH+); $^1$H NMR (CDCl$_3$): δ 1.20 (s, 3H), 1.50 (s, 3H), 1.52 (m, 2H), 1.61 (m, 4H), 2.65 (m, 2H), 2.78 (m, 2H), 3.20 (bs, 1H, exchanges with D$_2$O), 3.55 (d, J=9.3 Hz, 1H), 3.68 (d, J=9.3 Hz, 1H), 6.58 (d, J=5.4 Hz, 1H) and 7.04 (d, J=5.4 Hz, 1H).

Anal. calcd. for C$_{14}$H$_{21}$NO$_2$S: C, 62.89; H, 7.92; N, 5.23; S, 11.99. Found: C, 62.86; H, 8.10; N, 5.23; S, 12.12.

EXAMPLE 24

6-Benzoyloxy-5,6-dihydro-5,5-dimethyl-7-(2-oxopyrrolidin-1-yl)-7H-thieno[3,2-b]pyran A mixture of 5,6-dihydro-6-hydroxy-5,5-dimethyl-7-(2-oxopyrrolidin-1-yl)-7H-thieno[3,2-b]pyran (1.0 g, 3.74 mmol), benzoic anhydride (10 g) and 70% perchloric acid (10 drops) were heated to 80° C. for 2 h. The mixture was poured into ice water and extracted with dichloromethane and purified by flash chromatography using 1% methanol in dichloromethane as the eluant. The product was further purified by medium pressure chromatography using the same eluant, to give the product, 0.893 g (64%), as a grey solid: mp 130°-132°

C.; IR (KBr): 2981, 1721, 1695 and 1561 cm$^{-1}$; MS m/z 372 (MH+); $^1$H NMR (CDCl$_3$): δ 1.43 (s, 3H), 1.49 (s, 3H), 1.96 (m, 2H), 2.23 (m, 1H), 2.33 (m, 1H), 3.31 (m, 1H), 3.47 (m, 1H), 5.44 (d, J=9.3 Hz, 1H), 5.64 (d, J=9.3 Hz, 1H), 6.62 (d, J=5.3 Hz, 1H), 7.15 (d, J=5.3 Hz, 1H), 7.46 (t, J=7.4 Hz, 2H), 7.59 (t, J=7.4 Hz, 1H) and 8.03 (d, J=7.4 Hz, 2H).

Anal. calcd. for C$_{20}$H$_{21}$NO$_4$S: C, 64.67; H, 5.70; N, 3.77; S, 8.63. Found: C, 64.94; H, 5.57; N, 3.59; S, 8.64.

EXAMPLE 25

6-Hydroxy-5,5-dimethyl-7-(nicotinamido)-7H-thieno[3,2-b]pyran

The title compound was prepared as described for Example 3 starting with 6-bromo-5,6-dihydro-7-hydroxy-5,5-dimethyl7H-thieno[3,2-b]pyran (4.0 g, 15.2 mmol) and nicotinamide (3.7 g, 30.4 mmol) to give 1.1 g (24%): m.p. 248°-49° C.; IR (KBr): 3329, 3312, 1648, 1594, 1569 cm$^{-1}$ MS m/z 305 (MH+); $^1$H NMR (CDCl$_3$): δ 9.02 (s, 1H), 8.79 (d, J=5.6 Hz, 1H), 8.14 (d, J=5.6 Hz, 1H), 7.44 (m, 1H), 7.18 (d, J=5.4 Hz, 1H), 6.64 (d, J=5.4 Hz, 1H), 6.55 (d, J=5.6, 1H), 5.20 (m, 1H), 4.46 (brs, 1H), 3.81 (d, J=9.4 Hz, 1H), 1.50 (s, 3H), 1.36 (s, 3H).

Anal. Calcd. for C$_{15}$H$_{16}$N$_2$O$_3$S: C, 59.19; H, 5.30; N, 9.20. Found: C, 58.91; H, 5.10; N, 9.13.

EXAMPLE 26

6-Hydroxy-7-(2-imidazolidon-1-yl)-5,5-dimethyl-7H-thieno-[3,2-b]pyran

The title compound was prepared as described for Example 3 starting with 6-bromo-5,6-dihydro-7-hydroxy-5,5-dimethyl-7H-thieno[3,2-b]pyran (4.0 g, 15.2 mmol) and 2-imidazolidone (2.9 g, 30.4 mmol) to give 630 mg (15%): m.p. 156°-58° C.; IR (KBr): 3390, 1698, 1565, 1489 cm$^{-1}$; MS: m/z 309 (MH+); $^1$H NMR (CDCl$_3$): δ 7.13 (d, J=5.4 Hz, 1H), 6.54 (d, J=5.4 Hz, 1H), 5.15 (m, 1H), 4.67 (m, 2H), 3.79 (d, J=9.4 Hz, 1H), 3.24 (m, 2H), 1.48 (s, 3H), 1.31 (s, 3H).

Anal. Calcd. for C$_{12}$H$_{16}$N$_2$O$_3$S: C, 53.71; H, 6.01; N, 10.44. Found: C, 53.78; H, 6.14; N, 10.42.

EXAMPLE 27

6-Hydroxy-5,5-dimethyl-7-(isonicotinamido)-7H-thieno[3,2-b]-pyran

The title compound was prepared as described for Example 3 starting with 6-bromo-5,6-dihydro-7-hydroxy-5,5-dimethyl-7H-thieno[3,2-b]pyran (4.0 g, 15.2 mmol) and isonicotinamide (3.7 g, 30.4 mmol) to give 510 mg (11%): m.p. 223°-34° C.; IR (KBr): 3324, 3304,1649, 1569, 1536 cm$^{-+1}$; MS: m/z 305 (MH+); $^1$H NMR (CDCl$_3$): δ 8.78 cm$^{-1}$; MS: m/z 305 (MH+); $^1$H NMR (CDCl$_3$): δ 8.78 (d, J=5.8 Hz, 2H), 7.63 (d, J=5.8 Hz, 2H), 7.18 (d, J=5.4 Hz, 1H), 6.63 (d, J=5.4 Hz, 1H), 5.19 (m, 1H), 4.28 (brs, 1H), 3.79 (d, J=9.4 Hz, 1H), 1.49 (s, 3H), 1.35 (s, 3H).

Anal. calcd. for C$_{15}$H$_{16}$N$_2$O$_3$S: C, 59.19; H, 5.30; N, 9.20. Found: C, 58.85; H, 5.07; N, 9.05.

EXAMPLE 28

5,6-Dihydro-5,5-dimethyl-7-(pyrrolidin-1-yl)-7H-thieno[3,2-b]-pyran

A solution of 5,6-dihydro-5,5-dimethylthieno[3,2-b]pyran-7-one (1.0 g, 5,5 mmol), pyrrolidine (2.3ml, 27.4(mmol) sodium cyanoborohydride (0.345 g, 5.5 mmol) and 1N aqueous hydrochloric acid (5.5ml, 5.5 mmol) in methanol (15ml) was stirred at rt for 1 day. Additional sodium cyanoborohydride (0.345 g, 5.5 mmol) was added and the solution was stirred an additional 1 day; additional sodium cyanoborohydride (1.0 g, 15.9 mmol) was added again and the mixture stirred 5 additional days. The mixture was poured into water (100 ml) and extracted with dichloromethane. The dichloromethane solution was washed with water and dried over sodium sulfate. The solvent was evaporated in vacuo and the residue was purified by medium pressure chromatography using 2% methanol in dichloromethane as the eluant to give the product 0.70 g (54%) as a yellow solid; mp 49°-50° C.; IR(KBr): 2971, 1560 and 1394 cm$^{-1}$; MS:m/z 238 (MH+); $^1$H NMR (CDCl$_3$): δ 1.27(s,3H), 1.45(s3H), 1.80(m,4H), 1.91(m,2H), 2.76(m,4H), 4.09(m,1H), 6.57(d,J=5.4 Hz,1H), and 7.04(d,J=5.4 Hz,1H).

Anal. Calcd. for C$_{13}$H$_{19}$NOS:C,65.78; H,8.07; N,5.90. Found: C,65.35; H,8.24; N,5.97

EXAMPLE 29

7-(4-Cyanobenzamido)-5,6-dihydro-6-hydroxy-5,5-dimethyl-7H-thieno[3,2-b]pyran

The title compound was prepared as described in Example 3 starting with 6-bromo-7-hydroxy-5-6-dihydro-5,5-dimethyl-7H-thieno[3,2-b]pyran (6.73 g, 25.6 mmol), sodium hydride (2.14 g, 53.8 mmol), 4-cyanobenzamide (12.0 g, 82.1 mmol) and N,N-dimethylformamide (75 ml) to give the product, after recrystallization from dichloromethane and hexanes, 0.82 g (10%) as a colorless solid; mp 177°-178° C.; IR(KBr): 3420, 1648, 1545 and 1496 cm$^{-1}$; MS: m/z 329 (MH+); $^1$H NMR (CDCl$_3$): δ 1.35(s3H), 1.50(s,3H),3.79 (dd,J=7.8 Hz, J=2.5 Hz, 1H, simplifies to d, J=7.8 Hz with D$_2$O), 4.31 (d,J=2.5 Hz, 1H, exchanges with D$_2$O), 5.17 (m, 1H), 6.56(bd, J=6.8 Hz, 1H), 6.63(d,J=5.4 Hz, 1H), 7.18(d,J=5.4 Hz, 1H), 7.78 (d,J=8.2 Hz, 2H) and 7.91 (d, J=8.2 Hz,2H).

Anal. Calcd for C$_{17}$H$_{16}$N$_2$O$_3$S: C,62.18; H,4.91;N,8.53 S,9.75. Found: C,62.10; H, 4.74; N, 8.21; S,9.56.

EXAMPLE 30

6-Acetoxy-2-acetyl-7-(4-trifluoromethylbenzamido)-5,6-dihydro-5,5-dimethyl7H-thieno[3,2-b]pyran The title compound was prepared as described in Example 6 starting with 7-(4-trifluoromethylbenzamido)-5,6-dihydro-6-hydroxy-5,5-dimethyl-7H-thieno[3,2-b]pyran (1.5 g, 4.04 mmol), perchloric acid (70%, 10 drops) and acetic anhydride (20ml) to give the product after crystallization from dichloromethane and hexanes 0.382 g (21%) as a colorless solid; mp 225°-227° C.; IR (KBr):1755, 1668, 1654, 1541 and 1471 cm$^{-1}$; MS=m/z 456 (MH+);$^1$H NMR (CDCl$_3$): δ 1.41(s,3H), 1.43 (s,3H), 2.13 (s,3H), 2.47 (s,3H), 5.17 (d,J=9.3 Hz,1H), 5.42(m,1H), 6.77 (bd,J=7.9 Hz,1H), 7.14 (s,1H), 7.72 (d,J=8.3 Hz, 2H) and 7.88 (d,J=8.3 Hz,2H).

Anal. calcd. for C$_{21}$H$_{20}$F$_3$NO$_5$S: C,55.42; H,4.43; N,3.08. Found: C,55.06; H, 4.28; N,2.82

EXAMPLE 31

2-Acetyl-7-(4-trifluoromethylbenzamido)-5,6-dihydro-6-hydroxy-5,5-dimethyl-7H-thieno[3,2-b]pyran A mixture of potassium carbonate (92mg, 0.67 mmol) and 6-acetoxy-2-acetyl-7-(4-trifluoromethylbenzamido)-5,6-dihydro-5,5-dimethyl-7H-thieno[3,2-b]pyran (0.30 g, 0.66 mmol) in methanol was stirred at rt for 3h. The mixture was poured into ice water and a white solid crystallized within ten minutes. The solid was collected by filtration, washed with water, air dried and recrystallized from dichloromethane and hexanes to give the product 0.21 g (77%) as a colorless solid; mp 227°-229° C.; IR (KBr): 1652, 1541 and 1414 cm$^{-1}$; MS: m/z 414 (MH$^+$); $^1$H NMR (CDCl$_3$) $\delta$ 1.36 4.37(bs,1H exchanges with D$_2$O), 5.24 (m,1H), 6.61(bd,1H), 7.17(s,1H), 7.74 (d,J=8.2 Hz,2H) and 7.94 (d,J=8.2 Hz,2H).

Anal calcd. for c$_{19}$ H$_{18}$ F$_3$NO$_4$S: C,55.20; H,4.40; N,3.39. Found C, 55.21; H,4.21; N, 3.29.

EXAMPLE 32

5,6-Dihydro-6-methoxy-5,5-dimethyl-7-(2-oxopyrrolidin-1-yl)-7H-thieno[3,2-b]pyran 5,6-Dihydro-6-hydroxy-5,5-dimethyl-7-(2-oxypyrrolidin-1-yl)-7H-thieno[3,2-b]pyran (1.1 g, 4.11 mmol) was added to a mixture of sodium hydride (60% in mineral oil, 0.172 g, 4.32 mmol) in N,N-dimethylformamide (20ml) at 0° C. and stirred for 1.5h. Methyl iodide (0.28 ml, 4.52 mmol) was added to the resultant mixture and the mixture stirred at rt for 1 h. The mixture was poured into ice Water (100 ml) and extracted with dichloromethane. The dichloromethane solution was washed with water (5×) and dried over magnesium sulfate. The solvent was evaporated in vacuo and the residue was crystallized from dichloromethane and hexanes to give the product 0.825 g (71%) as a colorless solid; mp 117°-118° C.; IR(KBr): 2979, 1677, 1572 and 1420 cm$^{-1}$; MS: m/z 282 (MH$^+$); $^1$H NMR (CDCl$_3$): $\delta$ 1.27 (s,3H), 1.48(s,3H), 2.05(m,2H), 2.50(m,2H), 3.33(m,2H), 3.41(d,J=8.8 Hz, 1H), 3.51(s,3H), 5.33(d,J=8.8 Hz, 1H), 6.55(d,J=5.4 Hz, 1H) and 7.09 (d,J=5.4 Hz, 1H).

Anal Calcd. for C$_{14}$H$_{19}$NO$_3$: C,59.76; H,6.81; N,4.98. Found: C,59.73; H,6.46; N, 4.81.

EXAMPLE 33

7-Azido-5,6-dihydro-6-hydroxy-5,5-dimethyl-7H-thieno[3,2-b]-pyran.

Sodium Hydride (60% in oil, 3.77 g, 94.1 mmol) was added to a solution of 6-bromo-7-hydroxy-5,6-dihydro-5,5-dimethyl-7H-thieno [3,2-b]pyran (23.6 g, 89.7 mmol) in N,N-dimethyl formamide (275 ml) at 0° C. The mixture was stirred at rt for 1.5h and sodium azide (17.0 g, 0.269 mol) was added. The resultant mixture was stirred at rt for 3 days, then poured into ice water (1200 ml) and extracted with diethyl ether. The ether solution was washed with water (5×) and dried over magnesium sulfate. The solvent was evaporated in vacuo and the residue was purified by flash chromatography using 15% hexanes in dichloromethane as the eluant to give the product 5.1 g (25%) as a tan solid; mp 48°-50° C.; IR (KBr): 3471, 2104, 1568 and 1402 cm$^{-1}$; MS m/z 226(MH$^+$); $^1$H NMR (CDCl$_3$): $\delta$ 1.31 (s,3H), 1.47 (s,3H), 2.29 (d,J=5.8 Hz, 1H, exchanges with D$_2$O), 3.78(m,1H, simplifies to d, J=7.0 Hz, with D$_2$O), 4.44(d,J=7.0 Hz, 1H), 6.58 (d,J=5.4 Hz,1H) and 7.18 (d,J=5.4 Hz,1H).

Anal. Calcd. for C$_9$H$_{11}$N$_3$O$_2$S: C, 47.99; H,4.92; N,18.65. Found: C,48.36; H,4.91; N,18.12

EXAMPLE 34

7-Amino-5.6-dihydro-6-hydroxy-5,5-dimethyl-7H-thieno[3,2-b]-pyran

7-Azido-5,6-dihydro-6-hydroxy-5,5-dimethyl-7H-thieno[3,2-b]pyran (2.0 g, 8.88 mmol) Was added carefully in small portions to a mixture of lithium aluminum hydride (0.67 g, 17.8 mmol) in diethyl ether (40ml). The resultant mixture was stirred an additional 1 h at rt and quenched with successive dropwise addition of water (0.7 ml), 15% aqueous sodium hydroxide (0.7 ml) and water (2.0 ml). The aluminum salts were removed by filtration and the ether solution was dried over magnesium sulfate. The solvent was evaporated in vacuo to give the product 1.64 g (93%) as a beige solid; mp 111°-116° C.; IR(KBr):3110, 2971, 1565 and 1403 cm$^{-1}$; MS:m/z 200 (MH$^+$); $^1$H NMR (CDCl$_3$):$\delta$ 1.24(s,3H), 1.48(s,3H), 1.85(bs,3H, exchanges with D$_2$O), 3.38 (d,J=8.6 Hz,1H), 3.70 (d,J=8.6 Hz,1H), 6.55 (d,J=5.4 Hz,1H) and 7.07(d,J=5.4 Hz,1H).

Anal Calcd for C$_9$H$_{13}$NO$_2$S: C,54.25; H,6.58; N,7.03; S,1609. Found: C,54.80; H,6.23; N,6.44; S,15.91

EXAMPLE 35

7-(4-Fluorobenzamido)-5,6-dihydro-6-hydroxy-5,5-dimethyl-7H-thieno[3,2-b]pyran

A solution of 4-fluorobenzoyl chloride (0.91 ml, 7.72 mmol) in dichloromethane (5 ml) was slowly added to a solution of 7-amino-5,6-dihydro-6-hydroxy-5,5-dimethyl-7H-thieno[3,2-b]pyran (1.4 g, 7.03 mmol) and triethylamine (2.9 ml, 21.1 mmol) in dichloromethane (30 ml) at 0° C. The resultant mixture was stirred an additional Ih at 0° C., then washed with 1N hydrochloric acid, then with saturated aqueous sodium bicarbonate and dried over magnesium sulfate. The solvent was evaporated in vacuo and the residue was recrystallized from dichloromethane and hexanes to give the product 1.91 g (85%) as a colorless solid; mp 162°-164° C.; IR (KBr): 3365, 1648, 1604, 1535 and 1500 cm$^{-1}$; MS:m/z 322 (MH$^+$); $^1$H NMR (CDCl$_3$:$\delta$ 1.35(s,3H), 1.50(s,3H), 3.76(dd, J=2.0 Hz, J=7.9 Hz, 1H, simplifies to d,J=7.9 Hz, with D$_2$O), 4,72(d, J=2.0 Hz, 1H, exchanges with D$_2$O), 5.14 (m,1H), 6.45(bd,1H), 6.62 (d,J=5.4 Hz, 1H), 7.15 (m,3H), and 7.82 (m,2H).

Anal Calcd. for C$_{16}$H$_{16}$FNO$_3$S: C, 59.80; H,5.02, N,4.35. Found: C,59.81; H,5.07; N,4.18.

EXAMPLE 36

7-Benzamido-5,6-dihydro-6-hydroxy-5,5-dimethyl-7H-thieno-[3,2-b]pyran

The title compound was prepared as described in Example 34 starting with benzoyl chloride (0.95 ml), triethylamine (3.3 ml, 23 mmol) and 7-amino-5,6-dihydro-6-hydroxY-5,5-dimethyl-7H-thieno[3,2-b]pyran (1.55 g, 7.78 mmol) in dichloromethane (35 ml) to give the product 1.07 g (45%) as a colorless solid; mp 219°-220° C.; IR(KBr):3398, 1657, 1526 and 1490 cm$^{-1}$; MS:m/z 304 (MH$^+$); $^1$H NMR (DMSO-d$_6$):$\delta$ 1.21 (5,3H), 1.39 (5,3H), 3.81 (m,1H, simplifies to d, J=8.8 Hz, with D$_2$O), 5.00 (m,1H simplifies to d, 5=8.8 Hz, with D$_2$O), 5.61(d,J=6.0 Hz, 1H, exchanges with D$_2$O), 6.58(d,J=5.3 Hz,1H), 7.29(d,J=5.3 Hz,1H), 7.47(m,3H), 7.92(dd,J=1.3 Hz, J=8.2 Hz,2H) and 8.79 (d,J=8.3 Hz, 1H, exchanges with D$_2$O).

Anal. Calcd. for C₁₆H₁₇NO₃S: C,63.35; H,5.65; N,4.62; S,10.57. Found: C,63.12; H,5.28; N,4.24; S,10.37.

EXAMPLE 37

Antihypertensive Activity

Antihypertensive activity was assessed using a direct measurement of mean arterial blood pressure in spontaneously hypertensive rats (SHR). On the day of the experiment, catheters were implanted into the left carotid artery and the left jugular vein of SHR under light ether anesthesia. The catheters were exteriorized at the nape of the neck and secured with an adhesive wrap. Animals were then placed in stainless steel restraint cages in a quiet room and allowed at least 90 min post-surgical recovery before recordings were collected. Recordings of arterial pressure were obtained using a Statham pressure transducer connected to a Gould 2800 chart recorder. Groups of 4–6 SHR received a single oral dose of drug or vehicle (0.5% methylcellulose) administered by gavage at doses of 0.03 to 20 mg/kg. The percent reduction of mean arterial blood pressure compared to controls is reported.

EXAMPLE 38

Rb⁸⁶ Efflux from Smooth Muscle

Rabbit aorta are removed from freshly sacrificed animals. The vessels are cleaned and cut into small circular rings. The rings are placed onto stainless steel wires and immersed in a biological buffer (37° C.) bubbled with 95% $O_2$/5% $CO_2$. $Rb^{86}$ (4–5 μCi/mL) is added to 40–50 mL buffer containing all of the aortic rings. This loads each ring with an approximately equal amount of $Rb^{86}$. After 3–4 hours, sets of 2 rings are placed into 4 mL vials of fresh buffer. A background efflux rate is determined over a 30–40 minute period. Test compound is then added to a number of the vials (usually five) as the rings are moved through the 4 mL solutions over a set time period (usually 10 minutes). Finally, the rings are placed into the vials containing no test compound for a period of 10–20 minutes. At the completion of the experiment, the tissues are digested overnight in prostol before placing into scintillation cocktail to determine the total amount of radioactivity remaining within the tissues. An aliquot is removed from each of the efflux vials and quantitated in a liguid scintillation spectrometer. An efflux rate (or % change from pre-drug rates) is calculated and followed with time in the presence and absence of test compounds.

The pharmacological activity of the thienopyran derivatives is summarized below. Blood pressure reduction was measured in the spontaneously hypertensive rats (SHR). The efflux assay is a measure of potassium ion permeability changes within vascular smooth muscle cells.

TABLE

| | | Biological Activity of Thienopyran Derivatives | | | | | |
|---|---|---|---|---|---|---|---|
| EX. | NR₃R₄ | R₆ | R₂ | DOSE[a] | SHR[b] | DOSE[c] | %[d] |
| 1 | pyrrolidinon-1-yl | OH | H | 20 po | −55% | 100 | 25% |
| 4 | pyrrolidinon-1-yl | OH | 2-Br | 20 po | −43% | 100 | 90% |
| 5 | pyrrolidinon-1-yl | OH | 2-NO₂ | 20 po | −60% | 100 | 114% |
| 2 | piperidon-1-yl | OH | H | 20 po | −53% | 100 | 40% |
| 8 | pyrrolidinon-1-yl | OAc | H | 20 po | −10% | | |
| 6 | pyrrolidinon-1-yl | OAc | 2-Ac | 20 po | −33% | 100 | 23% |
| 7 | pyrrolidinon-1-yl | OH | 2-Ac | 20 po | −62% | 100 | 57% |
| 9 | p-NO₂PhCONH | OH | 2-NO₂ | 20 po | −29% | 100 | 30% |
| 17 | p-CF₃PhCONH | OH | 2-NO₂ | 20 po | −14% | | |
| 12 | p-NO₂PhCONH | OAc | 2-Ac | 20 po | −20% | | |
| 14 | p-ClPhCONH | OH | H | | | | |
| 13 | p-NO₂PhCONH | OH | 2-Ac | 20 po | −63% | 100 | 26% |
| 15 | p-ClPhCONH | OH | 2-NO₂ | 20 po | −42% | 100 | 39% |
| 19 | homopiperidinon-1-yl | OH | H | 20 po | −12% | | |
| 10 | piperidon-1-yl | OH | 2-NO₂ | 20 po | −65% | | |
| 24 | pyrrolidinon-1-yl | OBz | H | 20 po | −12% | | |
| 20 | homopiperidinon-1-yl | OH | 2-NO₂ | 20 po | −34% | | |
| 18 | pyrrolidin-1-yl | OH | H | 100 po | −48% | | |
| 11 | piperidon-1-yl | OH | 2-Br | 20 po | −64% | | |
| 21 | 2-oxohexamethylene-imin-1-yl | OAc | H | 20 po | −9% | | |
| 31 | p-CF₃PhCONH | OH | 2-Ac | 20 po | −26% | | |
| 35 | p-FPhCONH | OH | H | 20 po | −8% | | |

[a]Dose of test compound in groups of 3–6 spontaneously hypertensive rats (SHR) administered po. mg/kg
[b]% Decrease in mean arterial blood pressure compared to pretreatment control values
[c]Concentration of test compound in μM
[d]% Increase of Rb⁸⁶ efflux from smooth muscle.

What is claimed is:

1. A process for the preparation of a compound of the formula:

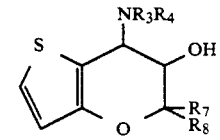

wherein,

R₃ and R₄ are hydrogen, C₂₋₅-alkanoyl, C₃₋₆cycloalkylcarbonyl, pyridylcarbonyl, and benzoyl (said benzoyl optionally substituted with nitor, halogen, trifluoromethyl, cyano, C₁₋₄-alkyl or C₁₋₄alkoxy), or NR₃R₄ together forms pyrrol, pyrrolidine, piperidine, pyrrolidinon-1-yl, piperidon-1-yl, homopiperidinon-1-yl, 2,5-dioxypiperazine, 2-imidazolidone or 2-oxyhexamethylenimine, and R₇ and R₈ are hydrogen or C₁₋₄alkyl, and optical isomers thereof, characterized by reacting a substituted thiophene having the formula:

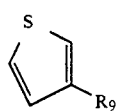

wherein R₉ is C₁₋₄-alkoxy, with an acryloyl chloride to provide a saturated ketone with the formula:

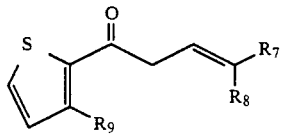

hydrolyzing the ketone with a hydrolyzing agent thereby forming a ketone having the formula:

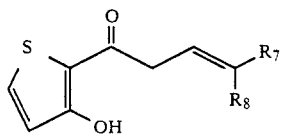

reacting the ketone with a protic acid to obtain a keto-thieno pyran having the formula:

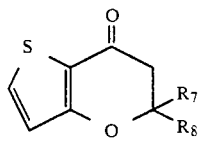

reducing the keto-thieno pyran with a reducing agent in order to obtain an alcohol having the formula:

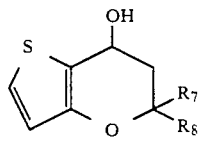

dehydrating the alcohol under acidic conditions to form an olefin having the formula:

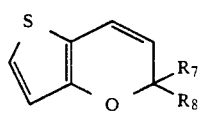

reacting the olefin with a hydrogen halogenating agent to obtain a halogen hydride having the formula:

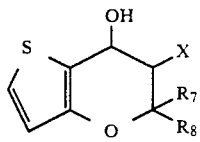

where X is bromine or chlorine, reacting the halogen hydride with a base to produce an epoxide having the formula:

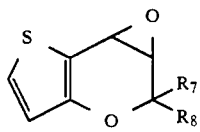

and,

A) reacting the epoxide with an amine or amide anion said amine or amide anion of the type formed by treating an amine or amide of the formula HNR₃R₄ with sodium hydride to produce substituted thienopyran(I) having the formula:

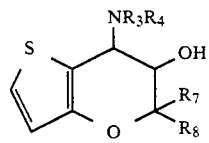

I or

B) reacting said epoxide with sodium azide and subsequently with a hydride reducing agent to produce substituted thienopyran(II) having the formula:

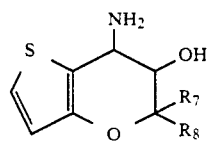

II said thienopyran(II) optionally acylated with a compound selected from the group consisting of C₂₋₅-alkanoyl chloride, C₃₋₆cycloalkylcarbonyl chloride, pyridylcarbonyl chloride, and benzoyl chloride (said benzoyl chloride optionally substituted with nitro, halogen, trifluoromethyl, cyano, C₁₋₄-alkyl or C₁₋₄alkoxy), to produce thienopyran(III) having the formula:

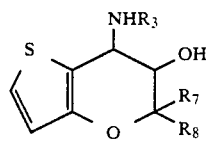

III

* * * * *